United States Patent [19]

Kellogg et al.

[11] 4,094,461
[45] June 13, 1978

[54] CENTRIFUGE COLLECTING CHAMBER

[75] Inventors: Robert Melroy Kellogg, Endwell; Alfred Paul Mulzet, Endicott, both of N.Y.

[73] Assignee: International Business Machines Corporation, Armonk, N.Y.

[21] Appl. No.: 810,243

[22] Filed: Jun. 27, 1977

[51] Int. Cl.² .............................................. B04B 11/06
[52] U.S. Cl. ...................................... 233/40; 233/44; 233/47 R
[58] Field of Search ..................... 233/27, 32, 34, 38, 233/40, 44, 46, 47 R, 21, 1 R, 7

[56] References Cited

U.S. PATENT DOCUMENTS

| | | | |
|---|---|---|---|
| 3,885,734 | 5/1975 | Lee | 233/7 X |
| 3,955,755 | 5/1976 | Breillatt et al. | 233/27 X |
| 4,007,871 | 2/1977 | Jones et al. | 233/27 |

Primary Examiner—George H. Krizmanich
Attorney, Agent, or Firm—Kenneth P. Johnson

[57] ABSTRACT

An improved collecting chamber for use with centrifuges for separating particles of different density suspended in a fluid, especially for separating the various fractions in human blood.

The chamber is provided with a partition or dam and a plurality of outlet tubes. These tubes are positioned so that they can draw off the various separated components of the blood. The divider prevents the mixing of the fractions after they enter the chamber. By properly regulating the output flow of the lines containing the packed red cells, and the plasma and red cells, the content of the buffy collect line is defined and can be maintained constant over relatively long periods of time without operator intervention.

12 Claims, 3 Drawing Figures

CENTRIFUGE COLLECTING CHAMBER

BACKGROUND OF THE INVENTION

Portions of the material herein disclosed have been disclosed and claimed in a copending patent application Ser. No. 803,907, filed June 3, 1977, by R. M. Kellogg, et al entitled "Centrifuge Assembly" and assigned to the assignee of this application.

Centrifuge bags are known in the art which are disposable, being used once and discarded. These previously known devices do not provide proper efficiency and are difficult to fabricate, involving complicated molding apparatus. These devices did not contemplate collection chambers which act in a selfregulatory manner.

DESCRIPTION OF PRIOR ART

Disposable centrifuge bags are disclosed, for example, U.S. Pat. Nos. 4,007,871 and 4,010,894. These bags require relatively complex forming apparatus, and moveover the collecting chambers of these bags do not provide sharp demarcations in the blood fraction levels. More importantly, these structures do not contemplate any self-regulatory action.

SUMMARY OF THE INVENTION

It is a general object of this invention to provide an improved collection chamber for use with a centrifuge container.

A particular object of the invention is to provide an improved collection chamber for a blood centrifuge container which provides greater efficiency and ease of fabrication.

Another object of the invention is to provide an improved collection chamber which is arranged to operate in a self-regulatory manner to collect the various blood fractions.

The foregoing and other objects, features and advantages of the invention will be apparent from the following more particular description of a preferred embodiment of the invention, as illustrated in the accompanying drawings, and described in connection therewith in the annexed specification.

Briefly described, the improved collection chamber comprises a cavity portion and a cap portion, which are separately manufactured, as by molding, and then assembled as by cementing or heat sealing. The chamber thus formed is provided with at least one partition or dam extending from but not touching the inward wall of the chamber toward but not reaching the outer wall of the chamber, at the discharge end of the chamber. The inlet end of the chamber is connected to one end of a fluid container of circular form, the other end of which is provided with an inlet connection for the specimen fluid. Blood to be fractionated is supplied through a rotating seal through the inlet tube to the inlet end of the circular fluid container, and under the influence of centrifugal force is separated into layers comprising various fractions, the heavier particles moving radially outward in the circular fluid container. The layered blood flow enters the collecting chamber at the inlet end thereof and moves toward the discharge end of the chamber.

On the side of the dam next to the inlet end of the collection chamber, a first outlet tube is provided which extends through the cap portion and toward the outer wall of the cavity, opening into the chamber at a first predetermined distance from the outer wall of the cavity. The interface between the plasma and the red cells, constituting the buffy layer of white cells and/or platelets resides at this distance during operation of the centrifuge, so that the buffy layer is drawn off through this first outlet tube. On the opposite side of the dam or spillway, a second outlet tube is provided, opening at substantially the same distance from outward wall of the cavity as the first outlet tube. Mixed plasma and red cells are withdrawn through this tube. The dam is open near the inner and outer wall to permit flow of the plasma and red cells past the dam. A third tube is provided at the discharge end of the chamber which extends to a second predetermined distance from the outer wall of the chamber, through which packed red cells are removed.

The parts are preferably made of suitable plastic material, such as, for example, medical grade polyvinyl chloride (PVC).

DETAILED DESCRIPTION OF A PREFERRED EMBODIMENT

Figure 1:
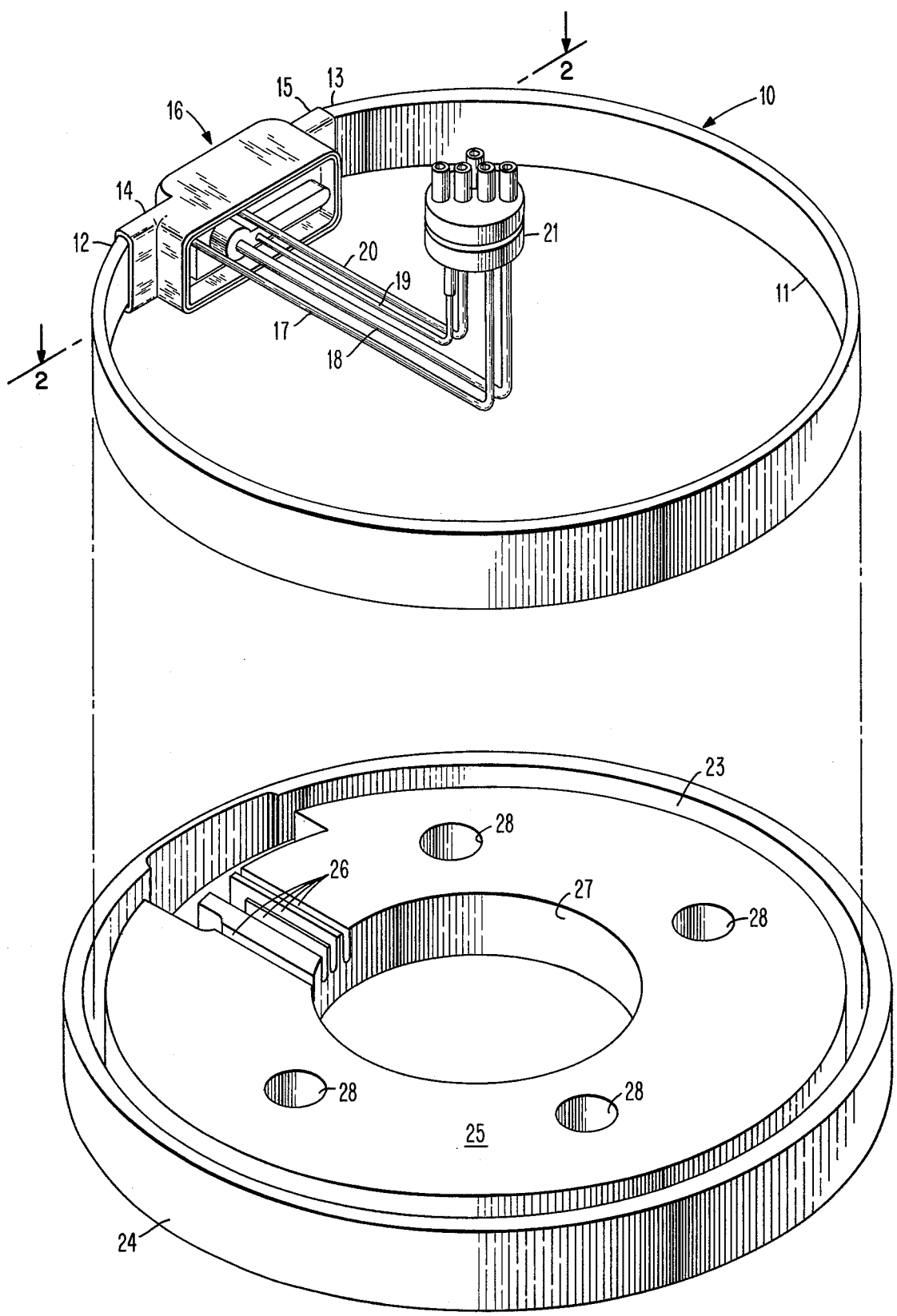
FIG. 1 is a diagrammatic perspective view showing a centriguge bowl, a filler or centerpiece and a fluid container in an exploded relation with the container having a collection chamber constructed in accordance with the invention.

Referring to FIG. 1, there is shown a blood container 10 which comprises a length of semi-rigid plastic tubing 11, preferably of medical grade polyvinyl chloride, and having a substantially rectangular cross-section. Tubing 11 serves as a separation channel and is formed in a circle as shown with ends 12, 13 joined to corresponding ends 14, 15 of a collection chamber 16 such as by cementing or heat sealing. The collection chamber 16 includes an internal barrier or wall, not shown, to isolate the input end 12 from the collection chamber. Fluid connections 17, 18, 19 and 20 to container 10 are made through a rotating seal 21 which may, for example, be the type shown in U.S. Pat. No. 3,489,145. Tubing connection 17 serves as an input connection and the remaining connections 18–20 serve as the outputs between the container and rotating seal.

Fluid container 10 is adapted for placement in a centrifuge to effect fractionation of input fluids such as whole blood. One such centrifuge arrangement is shown in FIG. 1 and comprises a bowl 24 and filler 25 which defines at its periphery in conjunction with the bowl a circular groove 23 into which tubing loop 11 and collection chamber 16 can be seated. Appropriate radial grooves 26 are formed in the filler to accommodate the tubes required for input and ouput connections with the rotating seal. Centrifuge bowl 24 may be formed of any suitable material such as metal or plastic or a combination of materials. The filler or centerpiece 25 can also be of a suitable material such as plastic, formed by molding or machining. It can be retained in place on central hub or plurality of distributed bosses or pins not shown. The filler piece has a central opening 27 which accommodates the seal and fluid connections. Holes 28 may be provided in the filler piece for convenience of lifting and also to serve as balancing holes for the cutouts accommodating the access tubing and collection chamber.

Figure 3:
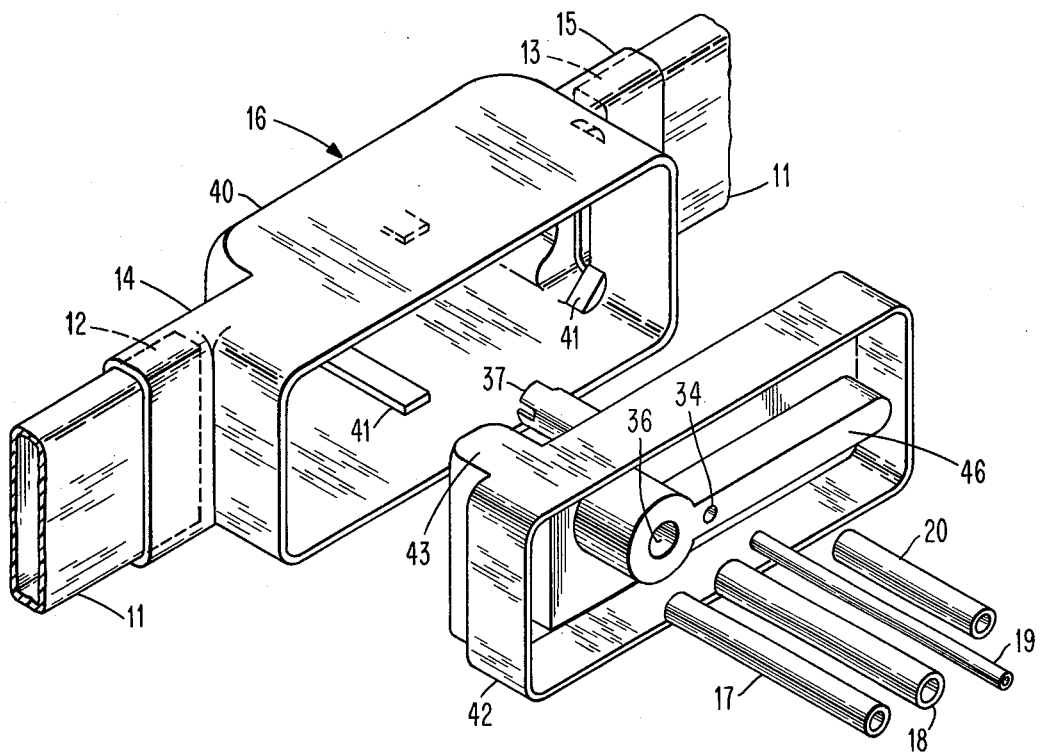
FIG. 3 is a diagrammatic view of the collection chamber of FIG. 1 in an exploded view showing the components thereof in greater detail.
Figure 2:
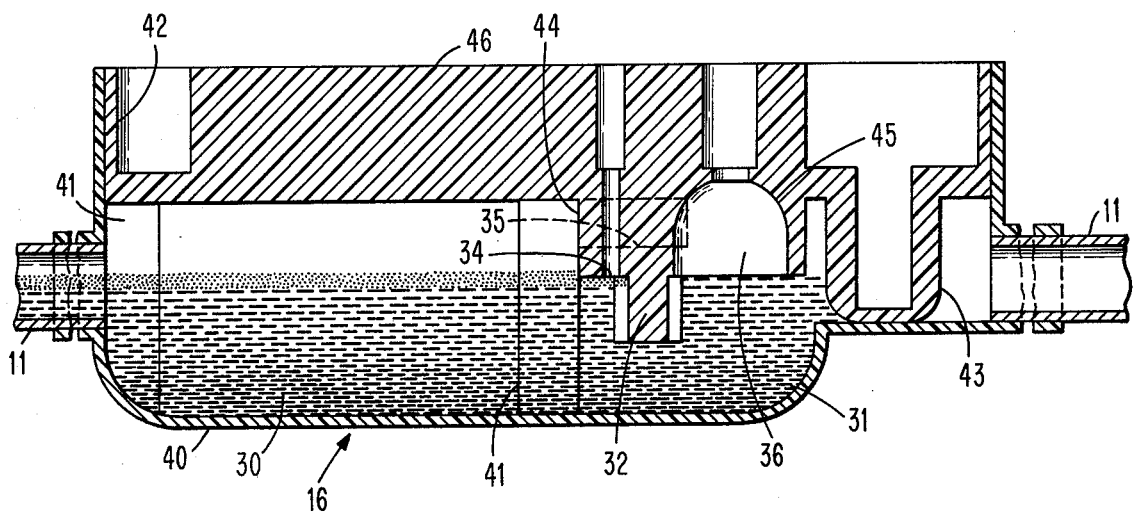
FIG. 2 is a sectional plan view of the collection chamber of FIG. 1 taken along the line 2—2.

The collection chamber 16, shown in greater detail in FIGS. 2 and 3, is constructed to permit the selective and concurrent withdrawal of the several fractions resulting from the centrifugation of the specimen input fluid. When centrifuging whole blood, the collect in the cavity forms three distinct fractions; at the outside, due to greatest density are the red blood cells, then next with less density is the buffy layer containing the white blood cells and platelets in a narrow band, while the innermost and least dense layer is the plasma.

The usual purpose for this centrifugation of blood is to collect the buffy layer with utmost efficiency. Such collection requires accurately maintaining the red cell-plasma interface, at which the white cells gather, coincident with the white cell collect and withdrawal port for removal. This is done in accordance with the present invention by dividing the cavity into first and second interconnected compartments and providing a withdrawal port for combined red cells and plasma which is effective to maintain the desired location of that interface buffy layer.

Referring to FIG. 2, the collection chamber 16 is shown in cross-section along a line 2—2 of FIG. 1. In this figure, the red cell fraction is indicated by dashes, the buffy layer with the white cells is indicated by stippling and the plasma is represented by the clear area. The collection chamber is formed into first and second interconnected compartments 30, 31 by a dam 32 between the top and bottom surfaces of the chamber and intercepting and blocking any flow to the right by the white cell interface or intermediate layer. White cells and platelets accumulating at this level are removed by vacuum applied at the white cell collect port 34. The dam as can be seen permits free movement of the red cell fraction into either compartment. The plasma can also freely move into the second compartment by openings both above amd below the white cell collect port, one such opening 35 being indicated by dotted lines. In second compartment 31, there is provided a collect port 36 for removal of the combined red cell and plasma fractions. Opening 35 pemits the plasma to flow around and then under the edge of the combined collect port for removal with the red cells. It is to be noted that this collect port extends into the collection chamber to approximately the same level as does collect port 34 for the white cells, and is effective to maintain the location of the white cell interface at the position illustrated. Its removal capacity is larger than port 34 in approximate proportion to the fraction quantities present. Some variation in removal flow rates can be achieved with the adjustment of applied vacuum.

During centrifugation of the blood, separation is produced due to the gravitational forces created by the rotation. The white cells accumulate at the red cell-plasma interface in compartment 30 but are blocked from movement to the right by the dam and are evacuated at the collect port 34. However, red cells and plasma are free to flow into second compartment 31 and form an interface there substantially devoid of white cells. Red cell-plasma collect port 36, since it extends into the cavity at the same depth as its counterpart for the white cells, is operable to maintain the interface in a fixed location, thus insuring highly efficient white cell removal. This arrangement avoids the continual manual adjustment withdrawal rates among the several ports heretofore used to maintain the position of the white cell layer.

The collection chamber configuration of FIG. 2 exhibits a time-dependent phenomeon due to a density stratification of the red cells in the red cell by-pass between first and second compartments 30, 31. As the red cells are in process, the denser cells accummulate on the outermost wall (bottom wall in FIG. 2) of the by-pass and reduce the active width of the by-pass thus impeding the red cell flow to the red-cell plasma collect port 36. The progressive choking off of the red cell flow causes the red cell-plasma interface to move radially inward which destroys the automatic control function of the two collinear collect ports 34, 36. Sedimentation of the red cells against the outside wall is avoided by adding a "packed red cell" removal port 37 (FIG. 3). This port is positioned as far outward radially as possible so that any high density red cells can be withdrawn, thus preventing occlusion of the by-pass.

The packed red cell removal port adds a further degree of quality control and flexibility to the automatic function of collect ports 34 and 36. A criterion in defining the quality of the collect is the degree of red cell contamination. By increasing the flow in the packed red cell line, the red cell-plasma interface can be moved radially a fraction of a millimeter and the degree of contamination in the collect can be minimized. The flow of the packed red cell line can be set so that the white cell collect has an optimum ratio of white cells to red cells and the system can be run without operator intervention for a relatively long time.

The separation channel 11 and collection chamber 16 of the present invention are readily fabricated by inexpensive molding techniques and permit disposal of the entire assembly after single use. For example, the separation channel can be a continuous extrusion, while the collection chamber can be molded in two pieces as illustrated in FIG. 3. Considering FIGS. 2 and 3 together, a base or cavity element 40 has openings at opposite ends 14, 15 to receive the two ends 12, 13 from the loop of separation channel and also has integrally formed stops 41 for locating the cap portion 42 which is inserted within the base. The bottom of the cap has a rectangular boss 43 which blocks the end of the separation channel upon assembly to prevent entry of inlet fluid into the collection chamber. The white cell dam 32 and bosses 44, 45 for the withdrawal or collect ports are integrally formed and extend beyond the top of the cap and may be part of a reinforcing rib 46. The port openings are formed with internal stops in counterbore fashion for limiting the insertion distance of the necessary tubes. After joining the cap, base, channel and tubing, the contacting surfaces are solvent-cemented or welded to form a unitary structure. This fabrication technique provides acurately positioned white blood cell and red cell-plasma collect ports to thus maintain the white blood cell interface at the proper location.

Usually the white cell collect port and plasma-red cell port extend into the collection chamber to approximately the same levels. Their relationship will, however, be determined by the specimen fluid and the level within the stratum of interest from which the collect is to be obtained. The ports can be relatively offset, if required, but adequate control has been found possible by altering the withdrawal rates among the outlet ports. Once set for a particular fluid the collection chamber function remains stable for extended periods of time.

While the invention has been particularly shown and described with reference to a preferred embodiment thereof, it will be understood by those skilled in the art that various changes in form and details may be made therein without departing from the spirit and scope of the invention.

What is claimed is:

1. Apparatus for continuous collection of an intermediate one of three or more stratified fractions of a liquid mixture at the outlet end of a centrifuge container comprising:

means forming a chamber;

a dam across said chamber for blocking flow only of one of said intermediate fractions;

first withdrawal port means extending interiorly of said chamber into the stratum of said blocked intermediate fraction; and second withdrawal port means at the downstream side of said dam extending into said chamber substantially the same distance as said first withdrawal port means whereby the location of said intermediate fraction is maintained having removal of the other of said fractions.

2. Apparatus as described in claim 1 further including a third withdrawal port extending into said chamber a distance sufficient to remove a portion of densest of said fractions.

3. Apparatus as described in claim 1 wherein said dam has an effective blocking thickness greater than the stratum of said selected intermediate fraction and extends transversely to the flow of said selected fraction.

4. Apparatus for continuous collection of blood fractions at the output end of a centrifuge container in which the red cell fraction and plasma fraction are separated by an intermediate fraction containing white cells and/or platelets comprising:

means forming a collection chamber;

dam means across said chamber for blocking flow of said intermediate fraction;

first withdrawal port means extending internally of said chamber into said intermediate fraction at the upstream side of said dam; and second withdrawal port means the downstream side of said dam extending internally of said chamber the same distance as said first withdrawal port means for removing a combination of said red cell and said plasma fractions.

5. Apparatus as described in claim 4 further including third withdrawal port means extending internally of said chamber into said red cell fraction for withdrawal of a portion thereof.

6. Apparatus as described in claim 1 further including means forming a circular separation channel of rectangular cross-section and having inlet and outlet ends each connected with said collection chamber, said collection chamber having means blocking flow of inlet liquid at the junction of said channel means.

7. Apparatus as described in claim 3 wherein said dam is integrally formed with said chamber forming means.

8. Apparatus as described in claim 3 wherein said chamber forming means and said separation channel means are formed of semi-rigid medical grade polyvinyl cloride.

9. Apparatus as described in claim 6 wherein said inlet end has port means for supplying liquid mixture to said separation channel.

10. A collection chamber for collecting blood fractions at the output end of a centrifuge container, in which red cells and plasma are separated by an interface containing a buffy coat, comprising:

two compartments, one for collecting plasma and red cells, and the other compartment collinearly located with respect to said one compartment and containing said buffy coat interface; and outlet ports for each of said compartments, said ports opening into said compartments at the nominal location of said buffy coat interface.

11. Apparatus as described in claim 10, further including an auxiliary outlet port for said one chamber for removal of said red cells.

12. Apparatus as described in claim 10 further including a partition between said two compartments effective to block flow only of said interface from said other compartment.

* * * * *